(12) United States Patent
Manassen et al.

(10) Patent No.: US 9,164,397 B2
(45) Date of Patent: Oct. 20, 2015

(54) OPTICS SYMMETRIZATION FOR METROLOGY

(75) Inventors: Amnon Manassen, Haifa (IL); Daniel Kandel, Aseret (IL); Moshe Baruch, Misgav (IL); Joel L. Seligson, Misgav (IL); Alexander Svizher, Haifa (IL); Guy Cohen, Misgav (IL); Efraim Rotem, Hod Hasharon (IL); Ohad Bachar, Timrat (IL); Daria Negri, Nesher (IL); Noam Sapiens, Bat Yam (IL)

(73) Assignee: KLA-Tencor Corporation, Milpitas, CA (US)

( * ) Notice: Subject to any disclaimer, the term of this patent is extended or adjusted under 35 U.S.C. 154(b) by 647 days.

(21) Appl. No.: 13/188,623

(22) Filed: Jul. 22, 2011

(65) Prior Publication Data
US 2012/0033226 A1     Feb. 9, 2012

Related U.S. Application Data

(60) Provisional application No. 61/370,347, filed on Aug. 3, 2010.

(51) Int. Cl.
*G01B 9/02* (2006.01)
*G03F 7/20* (2006.01)
*G01N 21/55* (2014.01)

(52) U.S. Cl.
CPC ............ *G03F 7/70633* (2013.01); *G01N 21/55* (2013.01); *G03F 7/70616* (2013.01)

(58) Field of Classification Search
CPC .................................................. G03F 7/70208
USPC .................................. 356/124–127, 399–401
See application file for complete search history.

(56) References Cited

U.S. PATENT DOCUMENTS

| | | | | |
|---|---|---|---|---|
| 3,345,912 A * | 10/1967 | Lohmann | ....................... | 356/520 |
| 4,355,871 A * | 10/1982 | Nevyas et al. | ................. | 351/212 |
| 4,642,701 A * | 2/1987 | Maeda et al. | .................. | 358/296 |
| 4,818,110 A | 4/1989 | Davidson | | |
| 5,048,926 A * | 9/1991 | Tanimoto | ................. | 359/485.07 |
| 5,363,170 A * | 11/1994 | Muraki | ........................... | 355/67 |
| 5,438,413 A * | 8/1995 | Mazor et al. | ................... | 356/508 |
| 5,468,580 A * | 11/1995 | Tanaka | ........................... | 430/22 |
| 5,760,408 A * | 6/1998 | Kikuchi et al. | ............. | 250/492.2 |
| 5,808,724 A * | 9/1998 | Ina et al. | ......................... | 355/53 |
| 5,978,021 A * | 11/1999 | Kim | ........................... | 348/218.1 |
| 6,172,349 B1 | 1/2001 | Katz et al. | | |

(Continued)

FOREIGN PATENT DOCUMENTS

| | | |
|---|---|---|
| JP | S6425120 A | 1/1989 |
| JP | 2007273954 A | 10/2007 |
| WO | 2005079498 A3 | 9/2005 |

*Primary Examiner* — Michael A Lyons
*Assistant Examiner* — Shawn Decenzo
(74) *Attorney, Agent, or Firm* — Suiter Swantz pc llo

(57) ABSTRACT

The present invention includes an illumination source, at least one illumination symmetrization module (ISM) configured to symmetrize at least a portion of light emanating from the illumination source, a first beam splitter configured to direct a first portion of light processed by the ISM along an object path to a surface of one or more specimens and a second portion of light processed by the ISM along a reference path, and a detector disposed along a primary optical axis, wherein the detector is configured to collect a portion of light reflected from the surface of the one or more specimens.

15 Claims, 13 Drawing Sheets

(56) References Cited

U.S. PATENT DOCUMENTS

| | | | |
|---|---|---|---|
| 6,549,267 B1* | 4/2003 | Kudo | 355/53 |
| 6,795,168 B2* | 9/2004 | Wang et al. | 355/67 |
| 6,906,805 B1* | 6/2005 | Ina et al. | 356/497 |
| 7,009,704 B1* | 3/2006 | Nikoonahad et al. | 356/401 |
| 7,317,531 B2* | 1/2008 | Mieher et al. | 356/401 |
| 7,386,830 B2* | 6/2008 | Fukuhara | 716/53 |
| 7,456,967 B2* | 11/2008 | Fukui et al. | 356/401 |
| 7,511,826 B2 | 3/2009 | Kreuzer | |
| 8,045,786 B2* | 10/2011 | Widmann et al. | 382/144 |
| 8,681,413 B2* | 3/2014 | Manassen et al. | 359/291 |
| 2004/0227944 A1* | 11/2004 | Fukui et al. | 356/401 |
| 2005/0200856 A1 | 9/2005 | Groot | |
| 2009/0086184 A1 | 4/2009 | Coston | |

* cited by examiner

OPTICS SYMMETRIZATION FOR METROLOGY

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional patent application entitled OPTICS SYMMETRIZATION FOR METROLOGY, naming Amnon Manassen, Daniel Kandel, Moshe Baruch, Joel Seligson, Alexander Svizher, Guy Cohen, Efraim Rotem, Ohad Bachar, Darla Negri and Noam Sapiens as inventor, filed Aug. 3, 2010, application Ser. No. 61/370,347.

TECHNICAL FIELD

The present invention generally relates to tool induced shift (TIS) measurement in optical metrology systems.

BACKGROUND

As the dimensions of semiconductor devices and components continue to decrease, the need for increased alignment control between various layers or features within a single layer of a given sample will continue to increase. In the context of semiconductor processing, semiconductor-based devices may be produced by fabricating a series of layers on a substrate, some or all of the layers including various structures. The relative position of these structures both within a single layer and with respect to structures in other layers is critical to the performance of the devices.

Metrology processes are used at various steps during a semiconductor manufacturing process to monitor and control one or more semiconductor layer processes. For example, metrology processes are used to measure one or more characteristics of a wafer, such as dimension (e.g., line width, thickness, etc.) of features formed on the wafer during a process step, wherein the quality of the process step can be determined by measuring the one or more characteristics. One such characteristic includes overlay error.

An overlay measurement generally specifies how accurately a first patterned layer aligns with respect to a second patterned layer disposed above or below it or how accurately a first pattern aligns with respect to a second pattern disposed on the same layer. The overlay error is typically determined with an overlay target having structures formed on one or more layers of a work piece (e.g., semiconductor wafer). If the layers or patterns of a given semiconductor device are not properly formed, then the structure on one layer or pattern tends to be offset or misaligned relative to the structure on the other layer or pattern. The misalignment between any of the patterns used at different stages of semiconductor integrated circuit manufacturing is known as 'overlay error.'

In a general sense, metrology applications, such as overlay measurements, require high quality optics in order to satisfy the requirements of advanced lithography processes. In the case of overlay metrology, optical imperfections (e.g., aberrations) in the optical components of an implementing system may result in Tool Induced Shift (TIS). In this manner, optical imperfections in an optical system may cause a shift in the measured overlay relative to the actual overlay. For example, optical aberrations present in an optical column of a metrology may lead to TIS. The standard measurement of TIS involves measuring overlay at first position and then rotating the wafer by 180 degrees and repeating the overlay measurement. As such, TIS may be defined as:

$$TIS = \frac{1}{2}[OVL(180°) + OVL(0°)] \quad \text{(Eq. 1)}$$

where $OVL(0°)$ represents the overlay measured at a first position and $OVL(180°)$ is the measured overlay following 180 degree rotation of the sample relative to the first position.

Conventionally, there exists two ways in which to eliminate or limit the existence of TIS. First, expensive high-end optical components may be utilized in an implementing metrology system in order to help avoid the optical imperfections which lead to TIS. Second, upon measuring TIS within a given system, the given system may be calibrated in order to correct for the observed TIS level. Due to the calibration requirements, the existence of TIS leads to reduced throughput of a given semiconductor fabrication process. Moreover, the need for high-end optical components in order to avoid or limit TIS leads to increased cost of semiconductor processing and metrology. Accordingly, it may be desirable to provide a method and/or system which provide a more efficient TIS measurement process as well as an improved optical system which reduces the amount of TIS in a given system.

SUMMARY

An apparatus suitable for illumination symmetrization is disclosed. In one aspect, an apparatus may include, but is not limited to, an illumination source; at least one illumination symmetrization module (ISM) configured to symmetrize at least a portion of light emanating from the illumination source; a first beam splitter configured to direct a first portion of light processed by the ISM along an object path to a surface of one or more specimens and a second portion of light processed by the ISM along a reference path; and a detector disposed along a primary optical axis, wherein the detector is configured to collect a portion of light reflected from the surface of the one or more specimens.

In another aspect, an apparatus suitable for measuring tool induced shift is disclosed. The apparatus may include, but is not limited to, an illumination source; a direct channel configured to transmit a first portion of light emanating from the illumination source to a surface of one or more specimens; a rotational channel configured to transmit a second portion of light emanating from the illumination source to a the surface of one or more specimens, wherein the rotational channel includes an optical rotation module configured to rotate the second portion of light by 180 degrees; a first shutter configured to selectively block an optical pathway of the rotational channel; a second shutter configured to selectively block an optical pathway of the direct channel; and a detector disposed, wherein the detector is configured to collect a portion of light reflected from the surface of the one or more specimens, wherein the portion of light includes at least one of light from the direct channel or light from the rotational channel.

In another aspect, an apparatus suitable for measuring tool induced shift is disclosed. The apparatus may include, but is not limited to, an illumination source; a direct channel configured to transmit a first portion of light emanating from the illumination source to a surface of one or more specimens; a rotational channel configured to transmit a second portion of light emanating from the illumination source to a the surface of one or more specimens, wherein the rotational channel includes an optical reflection module configured to rotate the second portion of light by 180 degrees; a first shutter configured to selectively block an optical pathway of the rotational channel; a second shutter configured to selectively block an optical pathway of the direct channel; and a detector, wherein the detector is configured to collect a portion of light reflected from the surface of the one or more specimens, wherein the portion of light includes at least one of light from the direct channel or light from the rotational channel.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring generally to FIGS. 1A through 4B, a system 100 suitable for providing illumination symmetrization is described in accordance with the present invention. In one aspect, the present invention is directed toward the symmetrization of illumination utilizing an illumination symmetrization module. The symmetrization of illumination in a metrology system acts to eliminate or limit tool induced shift (TIS) within a given system 100.

It is contemplated herein that the present invention may consist (but not required to consist) of adapting or reconfiguring presently existing microscopy systems. For instance, the present invention may consist of adapting the KLA-Tencor Archer 100 overlay control system. For example, an ISM may be inserted into a traditional system (e.g., Archer 100 system), whereby the ISM and associated adapted optics are placed between the illumination source and a beam splitter used for transmitting light along a reference path and object path of the system. It should be recognized that the present invention is not limited to an adaptation of an Archer 100 system, but rather the description above should be interpreted merely as an illustration. It is anticipated that the present invention may be extended to a wide variety of microscopy and overlay metrology systems.

Figure 1A:
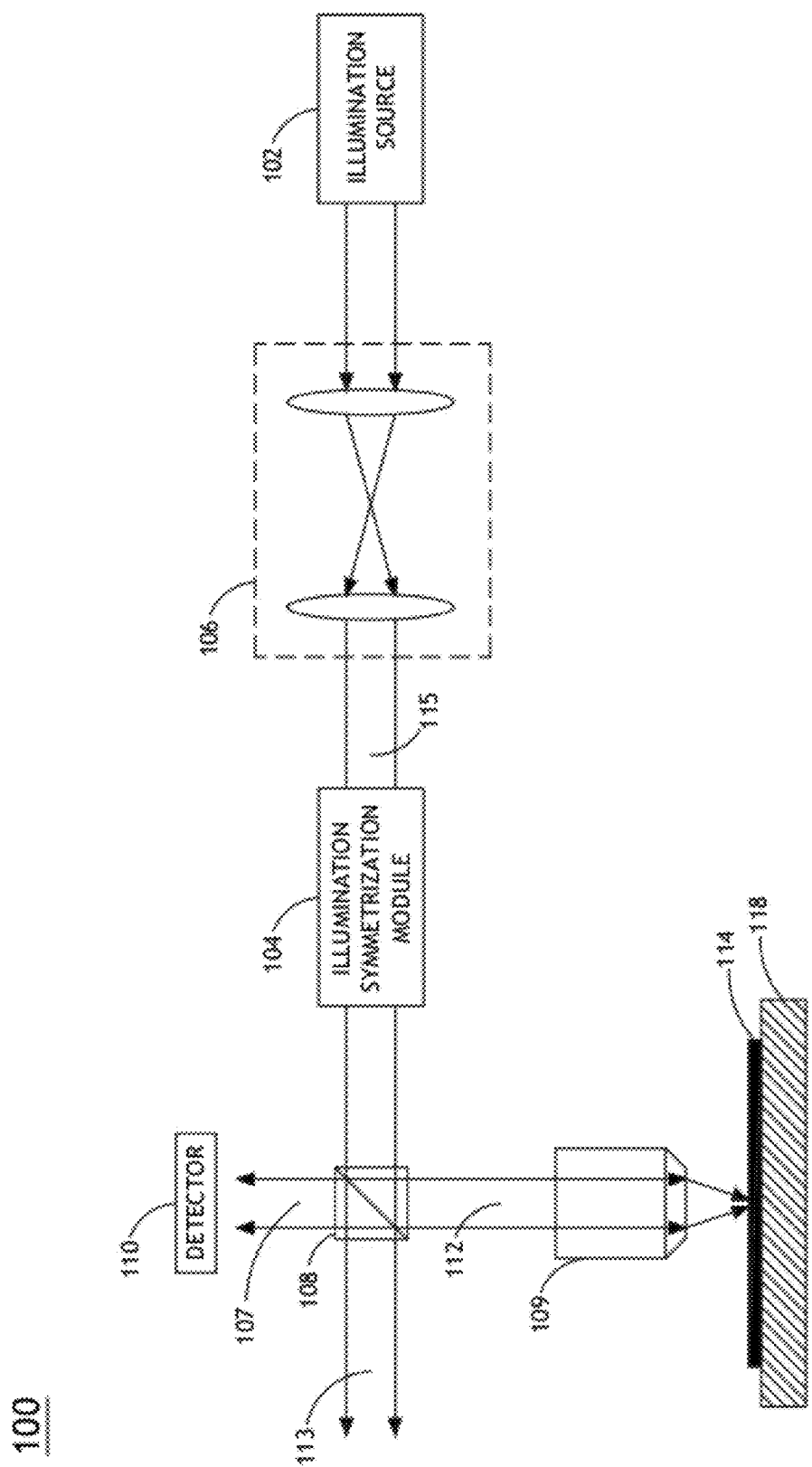
FIG. 1A illustrates a block diagram of an apparatus suitable for illumination symmetrization in accordance with the present invention.

Referring now to FIG. 1A, the system 100 suitable for illumination symmetrization may include an illumination source 102, an illumination symmetrization module 104, a first beam splitter 108, and a detector 110 disposed configured to receive light reflected from one or more specimens 114 (e.g., one or more wafers of a wafer lot).

In one aspect of the present invention, the illumination symmetrization module 104 is configured to symmetrize light emanating from the illumination source 102. For example, an illumination symmetrization module 104 may be disposed along an illumination path 115 such that light emanating from a light source 102 may be processed (i.e., symmetrized) by the illumination symmetrization module 104 and directed toward additional optics components (e.g., objective of object path 112, reference mirror of reference path 113, and detector 110) of the system 100. In a general sense, it should be recognized by those skilled in the art that an illumination symmetrization module 104 may be implemented within an overlay metrology system in order to improve the symmetry of light incident on a given specimen 114. The specific type of symmetrization operation to be carried out on light emanating from the illumination source 102 may depend on the specific illumination symmetry requirements of a given metrology application (e.g., overlay metrology, differential signal scatterometry overlay metrology, or optical critical dimension metrology). For instance, improved symmetry of illumination to 180° rotation may aid in reducing metrology tool induced shift (TIS) in overlay metrology measurements caused by optics imperfections. In another instance, improved reflection symmetry about a given axis (e.g., X-axis or Y-axis) may aid in achieving the desired level of reflection symmetry required in certain differential signal scatterometry overlay measurements.

Figure 1B:
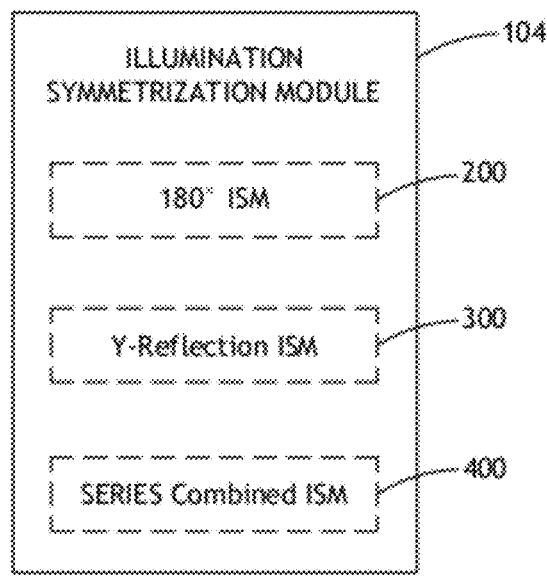
FIG. 1B illustrates a block diagram of types of illumination symmetrization modules suitable for implementation in accordance with the present invention.

Referring now to FIG. 1B, the illumination symmetrization module 104 of the system 100 may include, but is not limited to, a 180° degree rotation symmetrization module 200, a Y-reflection symmetrization module 300, a X-reflection symmetrization module (not shown), or a linear combination of one or more individual illumination symmetrization modules 400. Specific optical arrangements of these embodiments of the illumination symmetrization module 104, required to achieve specific desired illumination symmetrization operations, are discussed in greater detail further herein.

In one aspect of the present invention, a specimen 114 may be disposed on a specimen stage 118. In one embodiment, the specimen stage 118 may include a translatable stage (e.g., X-Y translatable stage) and/or rotatable stage (e.g., theta rotatable stage) controllable via a communicatively coupled computer system (not shown). The specimen 114 and stage 118 may be arranged such that the specimen 114 lies substantially perpendicular to the primary optical axis 107 of the system 100.

The illumination source 102 of the system 100 may include any illumination source known in the art. In one embodiment, the illumination source 102 may include a broadband light source (e.g., white light source). For example, the illumination source 102 may include, but is not limited to, a halogen light source (HLS). For instance, the halogen light source may include, but is not limited to, a tungsten based halogen lamp. In another example, the illumination source 102 may include a Xenon arc lamp. In another embodiment, the illumination source 102 may include a narrowband light source. For example, the illumination source 102 may include, but is not limited to, a laser light source.

In another aspect of the present invention, the first beam splitter 108 of the system 100 may split the light beam emanating from an illumination source 102, after passing through the ISM 104, into two paths: an object path 112 and a reference path 113. In this sense, the object path 112 and the reference path 113 of the system 100 may form a portion of a two beam interference optical system. For example, the first beam splitter 108 may direct a first portion of the beam of light from the illumination path 115 along the object path 112, while allowing a second portion of the beam of light from the illumination path 115 to be transmitted along the reference path 113. More specifically, the first beam splitter 108 may direct a portion of the light emanating from the illumination source 102, after passing through the illumination symmetrization module 104, to the surface of the specimen 114 (e.g., via object path 112) disposed on the specimen stage 114. Moreover, the first beam splitter 108 may transmit a second portion of the light emanating from the illumination source 102 to the components of the reference path 113. For instance, the beam splitter 108 may transmit a portion of light from the illumination path 115 along the reference path 113 to a reference mirror (not shown). It should be recognized by those skilled in the art that any beam splitter known in the art is suitable for implementation as the first beam splitter 108 of the present invention.

It should be apparent to those skilled in the art that the reference path 113 may include, but is not limited to, a reference mirror, a reference objective, and a shutter configured to selectively block the reference path 113. In a general sense, a two-beam interference optical system may be configured as a Linnik interferometer. Linnik interferometry is described generally in U.S. Pat. No. 4,818,110, issued on Apr. 4, 1989, and U.S. Pat. No. 6,172,349, issued on Jan. 9, 2001, which are incorporated herein by reference.

In another embodiment, the system 100 may include a main objective lens 109. The main objective lens 109 may aid in directing light along the object path 112 to the surface of the specimen 114 disposed on the specimen stage 118. For example, the beam splitter 108 may direct a portion of the light beam 115 emanating from the illumination source 102, after passing through the ISM 106, along the object path 112. Following the splitting process by the first beam splitter 108, the main objective lens 109 may focus light from the object path 112, which is collinear with the primary optical axis 107, onto the surface of the specimen 114. In a general sense, any objective lens known in the art may be suitable for implementation as the main objective lens 109 of the present invention.

Further, a portion of the light impinging on the surface of the specimen 114 may be reflected by the specimen 114 and directed along the primary optical axis 107 via the objective 109 and the beam splitter 108 toward the detector 110. It should be further recognized that intermediate optics devices such as intermediate lenses, additional beam splitters (e.g., a beam splitter configured to split off a portion of light to a focusing system), and imaging lenses may be placed between the objective 109 and the imaging plane of the detector 110.

In another aspect of the present invention, the detector 110 of the system 100 may be disposed along the primary optical axis 107 of the system 100. In this regard, the camera 110 may be arranged to collect imagery data from the surface of the specimen 102. For example, in a general sense, after reflecting from the surface of the specimen 114, light may travel along the primary optical axis 107 to the image plane of the detector 110 via the main objective 109 and the first beam splitter 108. It is recognized that any detector system known in the art is suitable for implementation in the present invention. For example, the detector 110 may include a charge coupled device (CCD) based camera system. By way of another example, the detector 110 may include a time delay integration (TDI)-CCD based camera system. In a further aspect, the detector 110 may be communicatively coupled with a computer system (not shown). In this regard, digitized imagery data may be transmitted from the detector 110 to the computer system via a signal, such as a wireline signal (e.g., copper line, fiber optic cable, and the like) or a wireless signal (e.g., wireless RF signal).

While the above description describes the detector 110 as being located along the primary optical axis 107 of the system 100, this characteristic should not be interpreted as a requirement. It is contemplated herein that the detector 110 may reside along an additional optical axis of the system 100. For example, in a general sense, one or more additional beam splitters may be utilized to divert a portion of light reflected from the surface of the specimen 114 and traveling along the object path 112 onto an additional optical axis. The camera 110 may be arranged such that light traveling along the additional optical axis impinges the image plane of the camera 110.

Figure 2A:
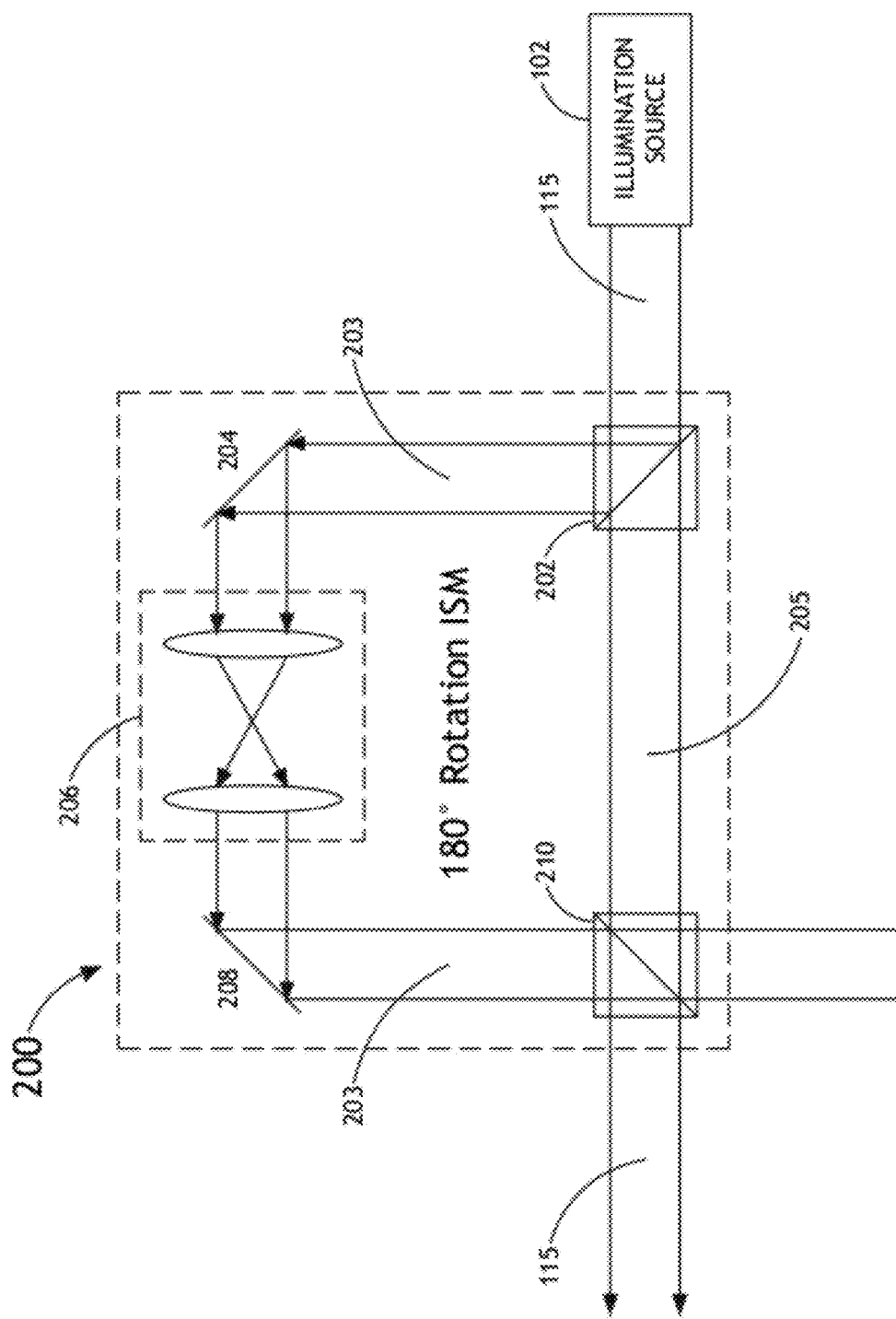
FIG. 2A illustrates a block diagram of a 180 degree rotation illumination symmetrization module in accordance with the present invention.
Figure 2B:
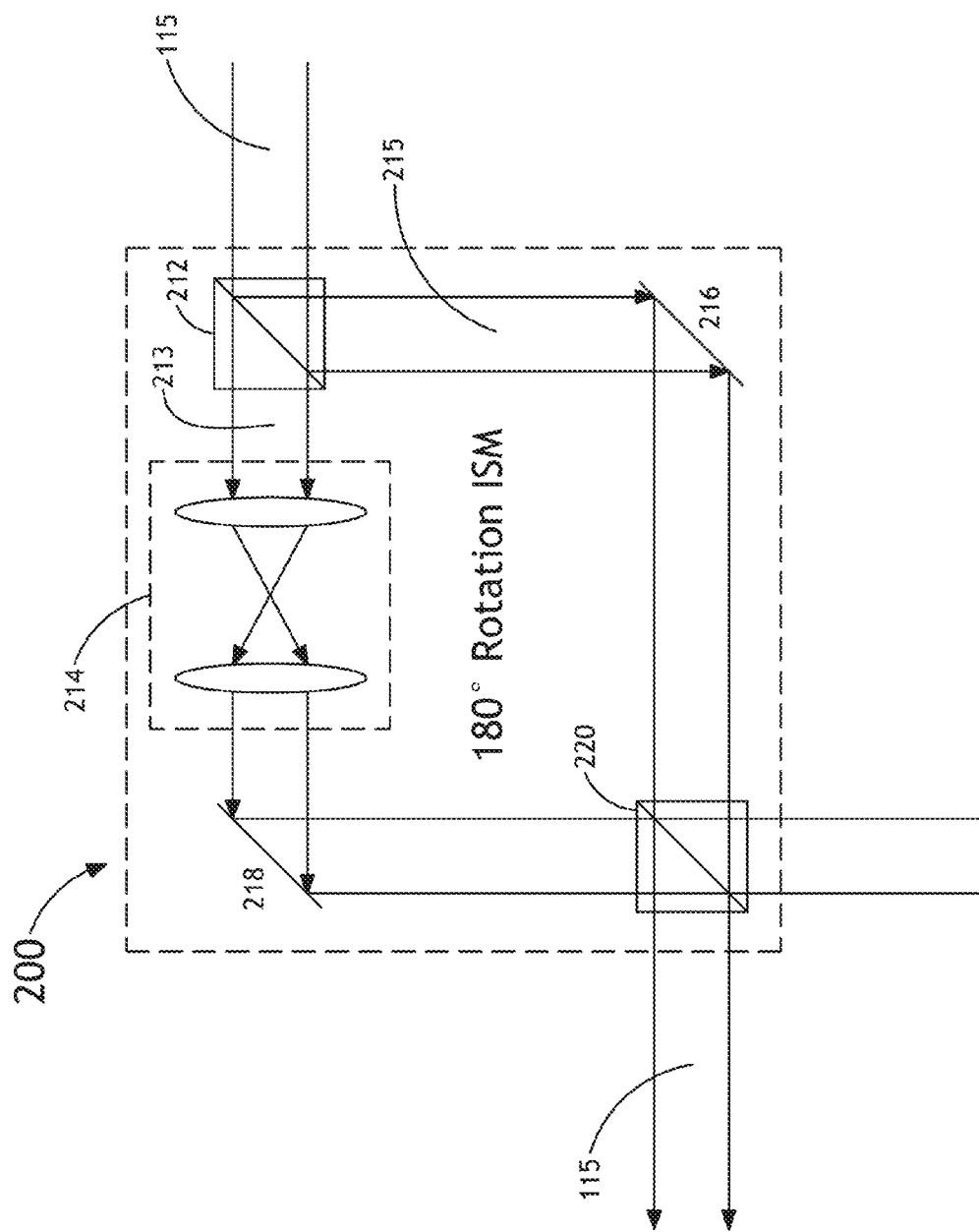
FIG. 2B illustrates a block diagram of a 180 degree rotation illumination symmetrization module in accordance with the present invention.

FIGS. 2A and 2B illustrate embodiments of illumination symmetrization modules 200 suitable for carrying out a 180° rotational symmetrization operation on light emanating from an illumination source 102. The 180° rotational symmetrization modules 200 illustrated in FIGS. 2A and 2B may act to improve the symmetry of processed light to rotation by 180°. In other terms, a 180° rotational symmetrization module 200 may act to transform light emanating from an illumination source 102 into illumination having an enhanced 180° degree rotationally symmetric character.

Referring now to FIG. 2A, an embodiment of the 180° illumination symmetrization module 200 is illustrated. The 180° illumination symmetrization module 200 of the present invention may include a rotational channel 203 defined by the pathway formed by a first beam splitter 202, a first mirror 204, a one-to-one imaging module 206, a second mirror 208, and a second beam splitter 210, and a direct channel 205 defined by the pathway formed by the first beam splitter 202 and the second beam splitter 210.

In one aspect, the first beam splitter 202 is arranged to divert a first portion of light from the illumination path 115 (i.e., emanating from the illumination source 102) toward a first mirror 204 along a rotational path 203 of the 180° ISM. The first beam splitter 202 is further configured to transmit a second portion of light along a direct path 205, which is substantially collinear with the illumination path 115 of the system 100, to a second beam splitter 210. Further, the first mirror 204 is arranged to direct a portion of light emerging from the first beam splitter 202 through a one-to-one imaging module 206 and toward a second mirror 208. The one-to-one imaging module 206 is configured to rotate the image by 180° with respect to the initial image, while simultaneously avoiding magnification of the image. The one-to-one imaging module 206 may include any set of optics devices, arrangements, and/or spacings of the optics devices known in the art suitable for achieving 180° rotation with one-to-one imaging.

Further, a second mirror 208 is arranged to direct light transmitted through the one-to-one rotational module 206 to the second beam splitter 210. The second beam splitter 210 of the 180° Rotation ISM 200 then combines light from the direct path 205 and light from the rotational path 203.

It should be recognized by those skilled in the art that light from the direct path 205 consists of non-rotated illumination, while light from the rotational channel 203 consists of illumination rotated by 180°. It should further be recognized that by combining the non-rotated light of the direct channel 205 and the 180° rotated illumination of the rotational channel 203 the light exiting the second beam splitter 210 (and being transmitted to first beam splitter 108 of the system 100) may possess improved rotational symmetry compared to the illumination inputted to the first beam splitter 202 of the 180° Rotation ISM 200. In a general sense, the applicant notes that the optical elements, such as mirrors and beam splitters, of the 180° Rotation ISM 200 described above may include any suitable optical elements known in the art.

Referring now to FIG. 2B, an alternative embodiment of the 180° Rotation ISM 200 is illustrated. The 180° Rotation ISM 200 of FIG. 2B may include a rotational channel 213 defined by the pathway formed by the first beam splitter 212, the one-to-one imaging module 214, a second mirror 218, and a second beam splitter 210, and a direct channel 215 defined by the first beam splitter 212, a second mirror 216, and the second beam splitter 220.

In a manner similar to that of the 180° Rotation ISM 200 depicted in FIG. 2A, the ISM 200 of FIG. 2B also acts to combine the non-rotated light of the direct channel 215 and the 180° rotated illumination of the rotational channel 213 utilizing the second beam splitter 220, resulting in improved rotational symmetry compared to the illumination inputted to the first beam splitter 212 of the 180° Rotation ISM 200. It should be further recognized that the alternative design illustrated in FIG. 2B allows for easy equalization of the optical path length of the rotational channel 213 and the direct channel 215.

Figure 3A:
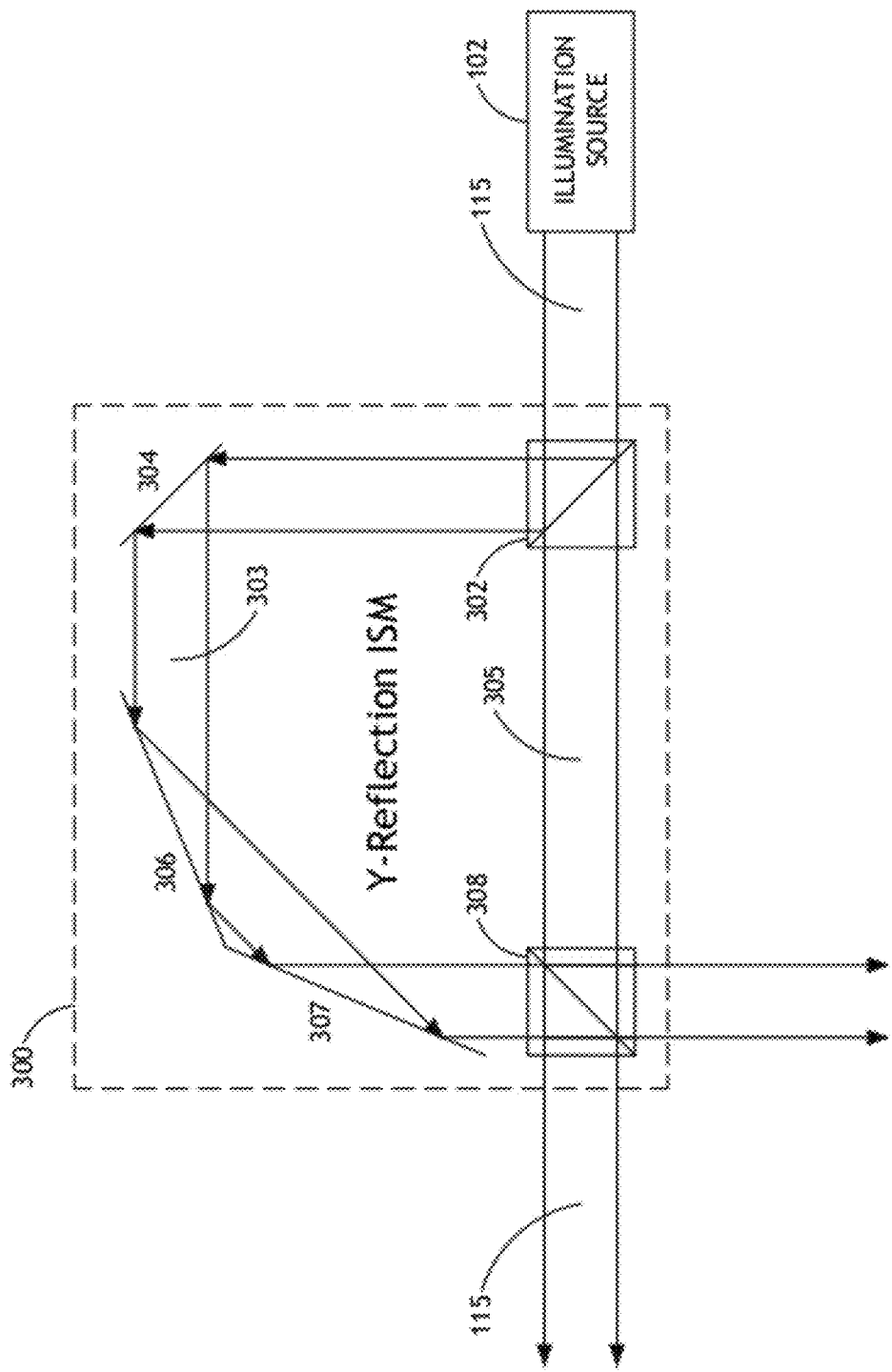
FIG. 3A illustrates a block diagram of a Y-reflection illumination symmetrization module in accordance with the present invention.

Referring now to FIG. 3A, one embodiment of the Y-reflection module 300 of the system 100 is illustrated. The Y-reflection module 300 may include a reflection channel 303 defined by the pathway formed by a first beam splitter 302, a first mirror 304, a pair of inverting mirrors 306, 307 and a second beam splitter 310, and a direct channel 305 defined by the pathway formed by the first beam splitter 302 and the second beam splitter 308.

In one aspect, the first beam splitter 302 is arranged to divert a first portion of light from the illumination path 115 toward a first mirror 304 along a reflection channel 303 of the Y reflection ISM 300. The first beam splitter 302 is further configured to transmit a second portion of light along a direct channel 305, which is substantially collinear with the illumination path 115 of the system 100, to a second beam splitter 308. Further, the first mirror 304 is arranged to direct a portion of light emerging from the first beam splitter 302 to a pair of inverting mirrors 306 and 307. The pair of inverting mirrors 306 and 307 are configured to invert the image about the Y-axis with respect to the initial image and direct the light reflecting from the surface of the inverting mirror 307 toward a second beam splitter 308. The pair of inverting mirrors 306 and 307 may include any set of optics devices, arrangements optics devices, and/or spacings of the optics devices known in the art suitable for image reflection about the Y-axis of the image plane.

Further, a second mirror 208 is arranged to direct light transmitted through the one-to-one rotational module 206 to the second beam splitter 210. The second beam splitter 210 of the 180° Rotation ISM 200 then combines light from the direct path 205 and light from the rotational path 203.

It should be recognized by those skilled in the art that light from the direct path 305 consists of non-inverted illumination, while light emerging from the reflection channel 303 consists of illumination reflected about the Y-axis. It should further be recognized that upon combining the non-inverted light of the direct channel 305 and the inverted illumination of the reflection channel 303 utilizing the second beam splitter 308, the light exiting the second beam splitter 308 (and being transmitted to beam splitter 108 of the system 100) may possess improved reflection symmetry about the Y-axis compared to the illumination inputted to the first beam splitter 302 of the Y-reflection ISM 300. In a general sense, the applicant notes that the optical elements, such as mirrors and beam splitters, of the Y-reflection ISM 300 described above may include any suitable optical elements known in the art.

Figure 3B:
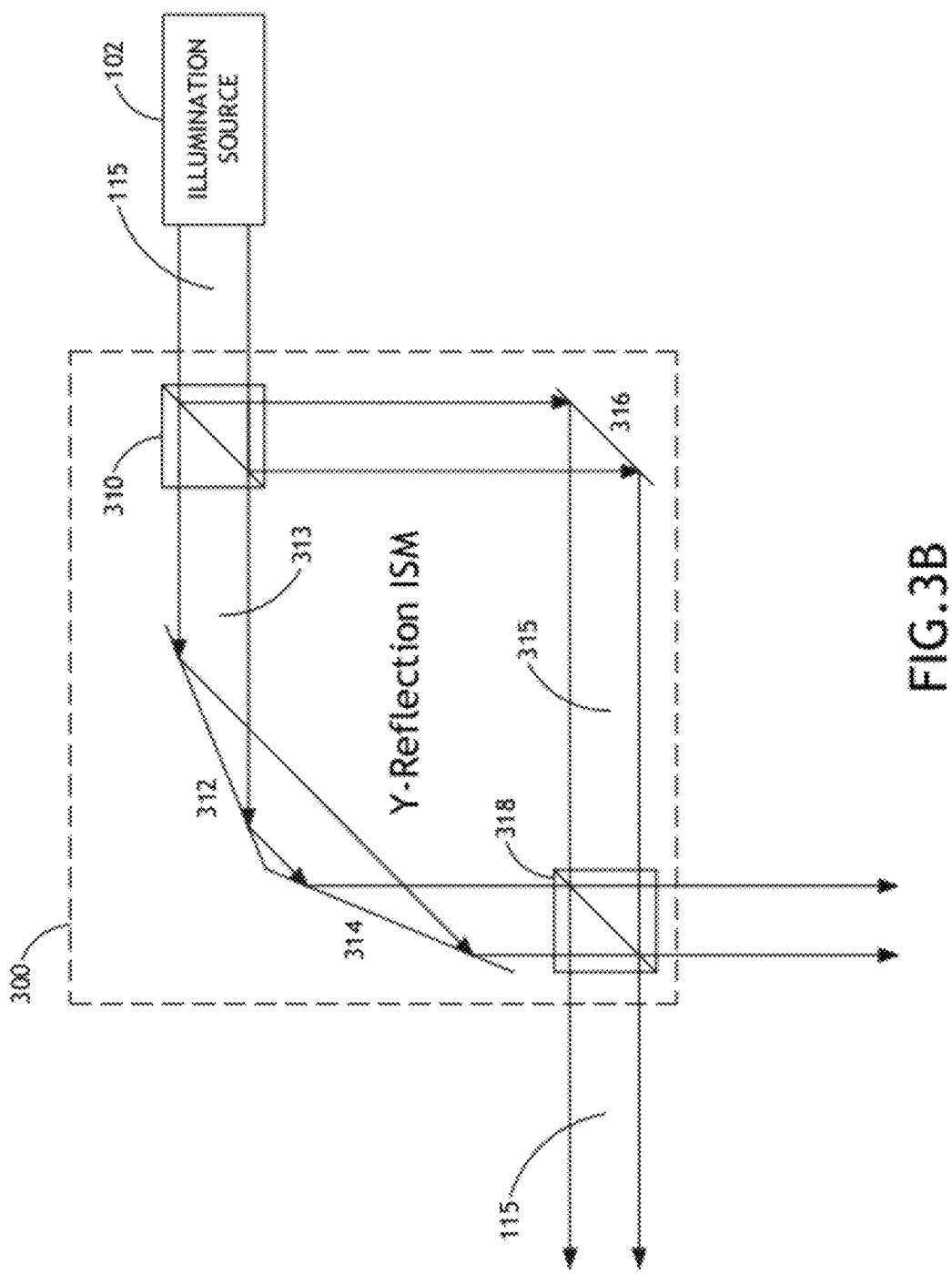
FIG. 3B illustrates a block diagram of a Y-reflection degree rotation illumination symmetrization module in accordance with the present invention.

Referring now to FIG. 3B, an alternative embodiment of the Y-reflection ISM 300 is illustrated. The Y-reflection module 300 of FIG. 3B may include a reflection channel 313 defined by the pathway formed by a first beam splitter 310, a pair of inverting mirrors 312, 314 and a second beam splitter 318, and a direct channel 315 defined by the pathway formed by the first beam splitter 310, a first mirror 316, and the second beam splitter 318.

In a manner similar to that of the Y-reflection ISM 300 depicted in FIG. 3A, the ISM 300 of FIG. 3B also acts to combine the non-inverted light of the direct channel 315 and the Y-inverted illumination of the reflection channel 313 utilizing the second beam splitter 318, resulting in improved reflection symmetry about the Y-axis compared to the illumination inputted to the first beam splitter 310 of the Y-reflection ISM 300. It should be further recognized that the alternative design illustrated in FIG. 3B allows for easy equalization of the optical path lengths of the reflection channel 313 and the direct channel 315.

It should be recognized that due to the design of the ISM modules 200 and 300 illustrated in FIGS. 2A, 2B, 3A, and 3B, approximately 50% of the illumination of the system 100 escapes the system and fails to reach the common beam splitter 108 of the system 100. It should be recognized that this loss in illumination may be substantially avoided if the second beam splitters (e.g., 210, 220, 308, and 318) of the ISMs 200 or 300 are replaced with flip-in mirrors (not shown). In this manner, the illumination of the transformation channel (e.g., 180° rotational channel 203, 215 or reflection channel 303, 313) and the direct channel (e.g., 205, 215, 305, 315) may be measured sequentially and the images collected from each measurement may be added together to form a composite image having a substantially improved symmetrization character (e.g., 180° rotational symmetry, Y-reflection symmetry, or X-reflection symmetry (not shown)). Applicant notes that any flip-in mirror system known in the art is suitable for implementation in the present invention.

Alternatively, the loss in light described above may also be avoided by replacing the first beam splitter (e.g., 202, 212, 302, 310) and the second beam splitter (e.g., 210, 220, 308, and 318) of a given ISM (e.g., 200 or 300) with two synchronized choppers. In this manner, the synchronized choppers act to pass light from each channel 50% of the time. For example, at given time 1, light is transmitted through a first chopper, while blocked at the second chopper. Then, at a time 2, light is blocked at the first chopper and transmitted by the second chopper. The resulting waveform passed on to the combined beam splitter 108 of the system 100 will then consist of alternating pulses of illumination from the transformation channel (e.g., 180° rotational channel 203, 215 or reflection channel 303, 313) and the direct channel (e.g., 205, 215, 305, 315). Applicant notes that any chopper system known in the art is suitable for implementation in the present invention.

Figure 4A:
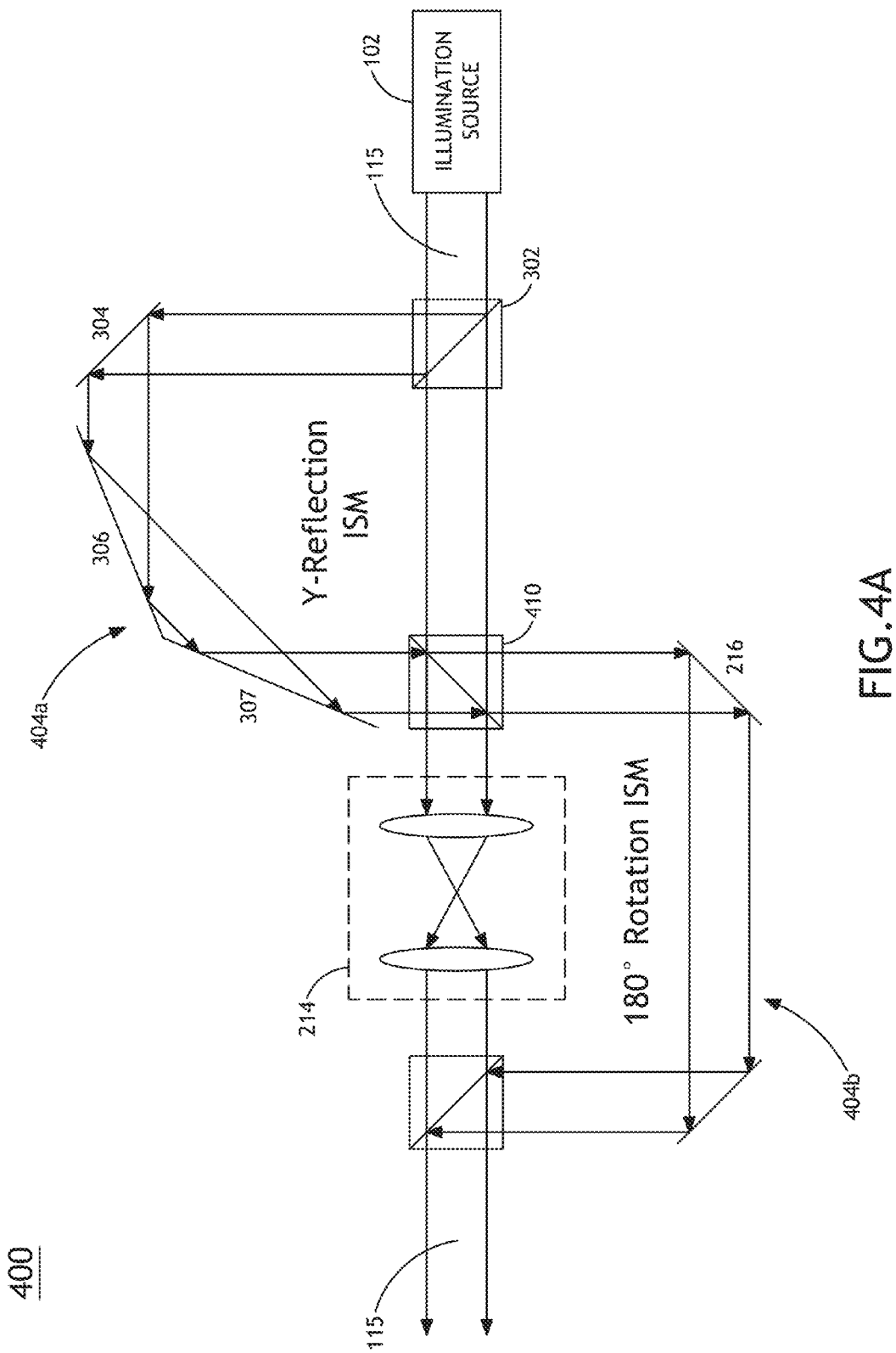
FIG. 4A illustrates a block diagram of a series combination of a Y-reflection degree rotation illumination symmetrization module and a 180 degree rotation illumination symmetrization module in accordance with the present invention.
Figure 4B:
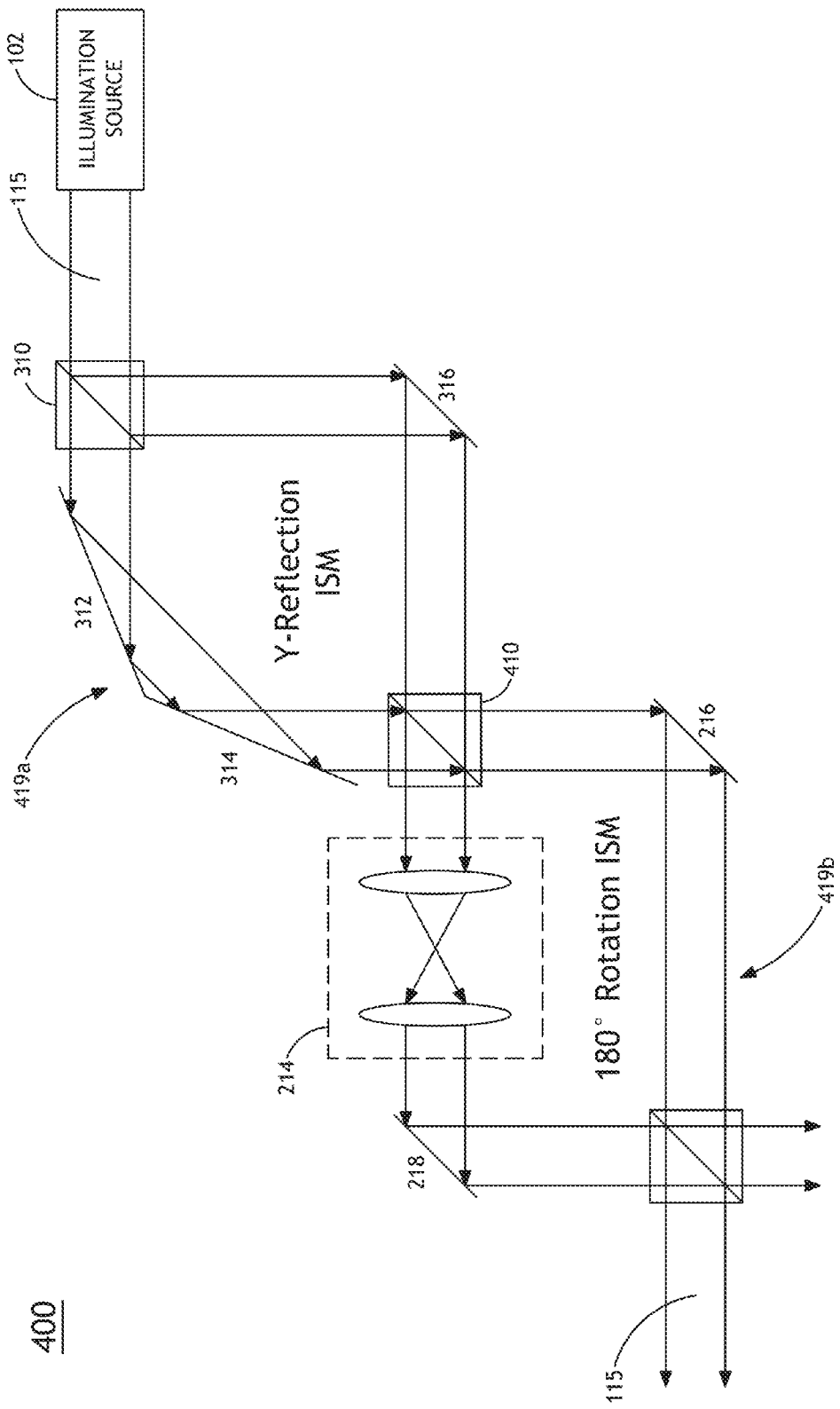
FIG. 4B illustrates a block diagram of a series combination of a Y-reflection degree rotation illumination symmetrization module and a 180 degree rotation illumination symmetrization module in accordance with the present invention.

FIGS. 4A and 4B illustrate embodiments 400 of linearly combined illumination symmetrization modules. Linear combinations of ISMs may be utilized in order to improve upon the level of symmetry in a given image or when more than one symmetrization process is required. For example, as shown in FIGS. 4A and 4B, a Y-reflection ISM (e.g., 404*a* or 419*a*) may be optically coupled (via beam splitter 410) in series with a 180° rotational ISM (e.g., 404*b* or 419*b*). For instance, light emanating from an illumination source 102 may first undergo a Y-reflection symmetrization process via Y-reflection ISM 404*a*. Upon exiting the Y-reflection ISM 404*a*, light may be transmitted from the common beam splitter 410 and enter the 180° rotational ISM 404*b*. It is recognized that light emerging from the 180° rotational ISM 404*b* will possess improved 180° rotation and Y-reflection symmetry.

Moreover, it is further contemplated that identical ISMs may be combined in series (not shown). For example, a first 180° rotational ISM may be optically coupled in series utilizing a common beam splitter with a second 180° rotational ISM. It is further anticipated that any number and type of ISM may be combined in series. Applicant notes that the utilization of identical series coupled ISMs may improve the level of symmetrization by up to 100-fold, depending on the number and type of ISMs implemented.

Further contemplated that two or more modules of the same type may be combined to further improve the illumination symmetry. Applicants note that a 100 fold increase in illumination symmetry may be achieved utilizing two series combined ISMs of the same symmetrization type.

It is noted that the above description of the various ISMS in FIG. 2A though 4B does not represent a set of limitations but rather should be interpreted as illustrative in nature. It is contemplated herein that a variety of additional illumination modules may be constructed, wherein the specific choice of illumination symmetrization module components may depend on the specific symmetry type required for a given application.

Referring generally to FIGS. 5A through 7, systems 500, 501, 600, and 700 suitable for tool induced shift measurement are described in accordance with the present invention. In one aspect, the present invention is directed toward a system which provides improved (tool induced shift) TIS measurement speeds. The utilization of faster TIS measurements may decrease the overall time required for TIS calibration, increasing throughput of a given semiconductor processing step.

Figure 5A:
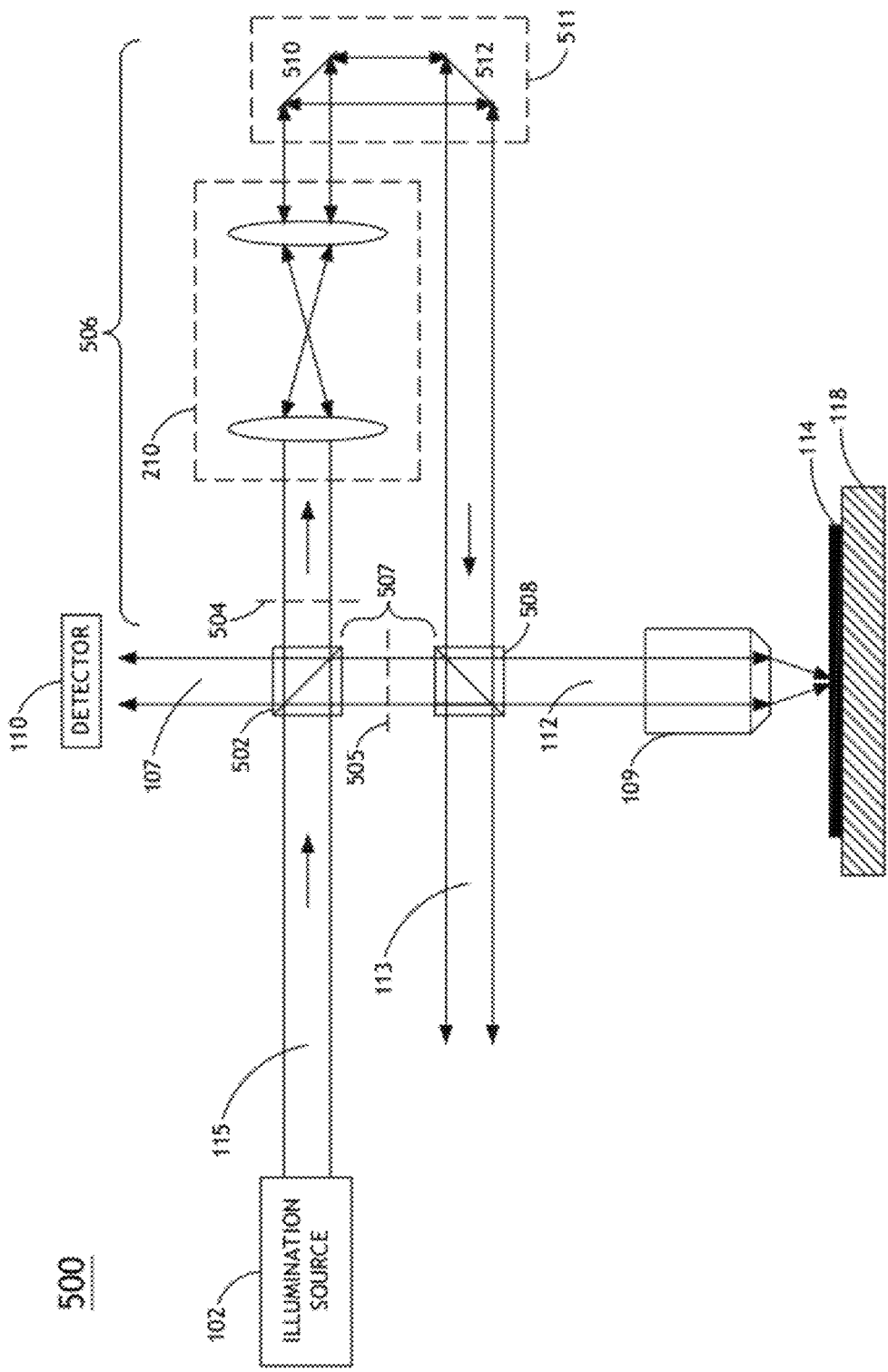
FIG. 5A illustrates a block diagram of an apparatus suitable for tool induced shift measurement in accordance with the present invention.
Figure 5B:
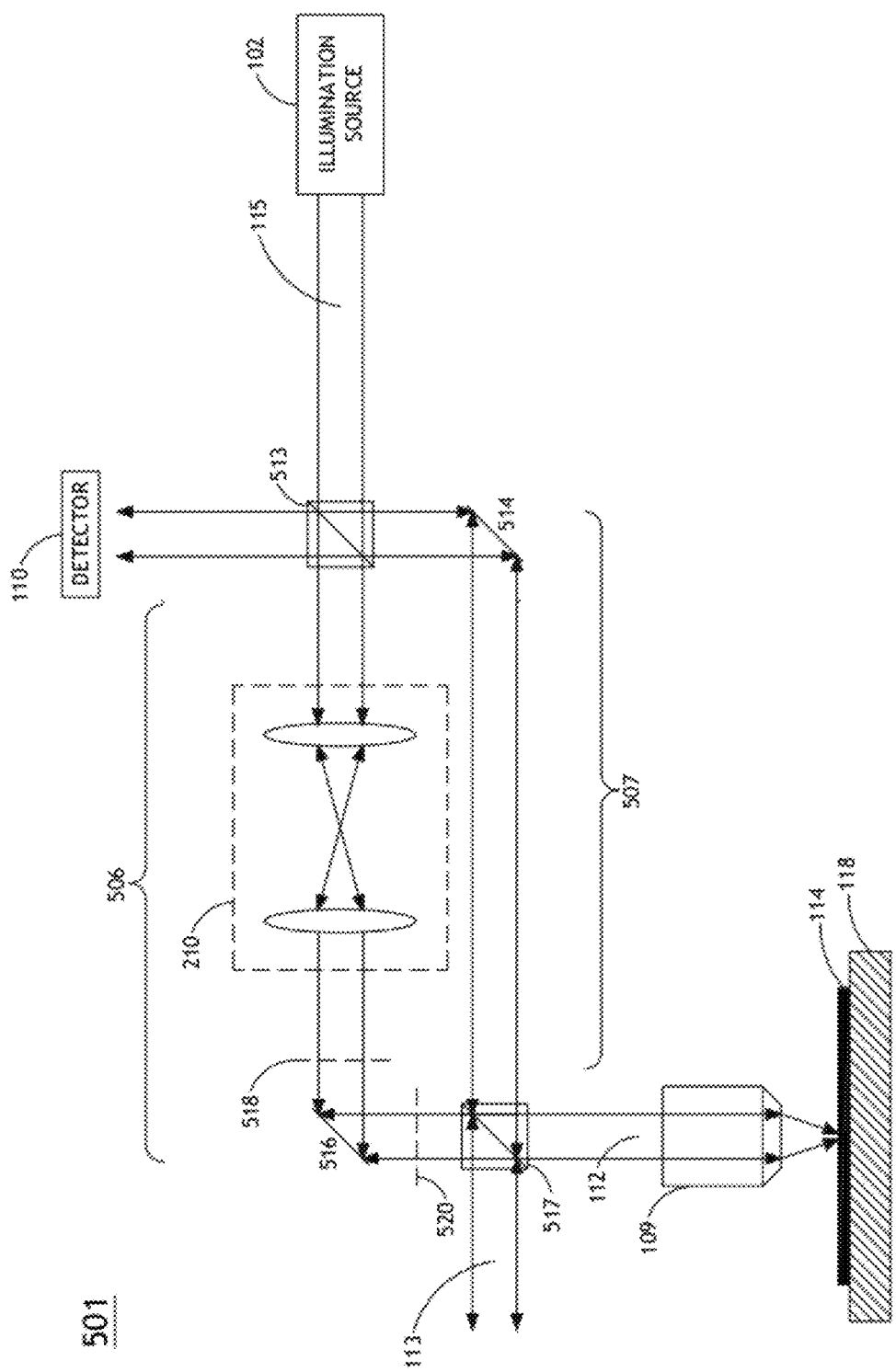
FIG. 5B illustrates a block diagram of an apparatus suitable for tool induced shift measurement in accordance with the present invention.

FIG. 5A and FIG. 5B illustrate embodiments of systems 500 and 501 suitable for tool induced shift measurement in accordance with the present invention.

Referring now to FIG. 5A, in one embodiment, the system 500 may include, but is not limited to, an illumination source 102, a detector 110, a rotational channel 506, a direct channel 507, a first shutter 504, and a second shutter 505. It is recognized herein that the description of an illumination source 102 and a detector 110 provided above with respect to FIG. 1A should be interpreted to apply throughout the remainder of the present disclosure.

In one aspect, the direct channel 507 of the system 500 is formed by the pathway defined by the first beam splitter 502 and the second beam splitter 508. It should be recognized that illumination emanating from an illumination source 102 may pass between a first beam splitter 502 and a second beam splitter 508 via either the rotational channel 506 or the direct channel 507.

In one embodiment, the first beam splitter 502 is arranged to direct a first portion of light from the illumination path 115 toward the second beam splitter 508 via the direct channel 507. It is noted that in the present embodiment the direct channel 507 is aligned substantially collinearly with the object path 112 (and the primary optical axis 107) of the system 500. The first beam splitter 502 is further configured to transmit a second portion of light from the illumination source 102 through a rotational module and toward an optical return module 511 via the rotational channel 506. Upon impinging on the return module 511 of the rotational channel 506 light traveling along the rotational channel 506 may be reflected toward a second beam splitter 508.

In one embodiment, the rotational module of the system 500 may include, but is not limited to, one or more one-to-one 180° rotation modules 210, as depicted in FIG. 5A. The one-to-one imaging module 210 may be configured to rotate the image by 180° with respect to the initial image, while simultaneously avoiding magnification of the image. The one-to-one imaging module 210 may include any set of optics devices, arrangements, and/or spacings of the optics devices known in the art suitable for achieving 180° rotation with one-to-one imaging. After passing through the one-to-one 180° rotation module 210, light in the rotational channel 506 may travel through the set of return optics of the optical return module 511, which act to redirect the light from the upper arm of the rotational channel 506 toward the second beam splitter 508 via the lower arm of the rotational channel 506.

In one embodiment, the return optics of the optical return module 511 may include, but are not limited to, a first mirror 510 and a second mirror 512. The first mirror 510 may be configured to reflect light transmitted through the one-to-one 180° rotation module 210 toward the second mirror 512. The second mirror 512 may be arranged to reflect light received from the first mirror 510 toward the second beam splitter 508. In a further embodiment, as depicted in FIG. 5A, the first mirror 510 and the second mirror 512 of the return optics module 511 may consist of substantially planar mirrors.

In another aspect, the first shutter 504 may be configured to selectively block the optical path of the rotational channel 506. In this manner, the system 500 may act to selectively block light from the illumination source 102 from being transmitted through the rotational channel 504. In the same manner, a second shutter 505 may be configured to selectively block the optical path of the direct channel 507. In this manner, the system 500 may act to selectively block light from the being transmitted from the illumination source 102 through the direct channel 507.

In one embodiment, it is contemplated herein that the first shutter 504 and the second shutter 505 may include shutters capable of opening and closing within 10 ms. It is further recognized herein that any appropriate shutter system known in the art may be utilized as the first shutter 505 and/or second shutter 505 of the present invention.

It is an aspect of this invention that the utilized optical pathway between the first beam splitter 502 and the second beam splitter 508 may be selected via the conjunctive control of the first shutter 505 and the second shutter 505. In a first configuration, when shutter 505 is open (i.e., direct channel is open) and shutter 504 is closed (i.e., rotational channel is blocked), the system 500 operates as a standard imaging microscope. In this manner, light from the illumination path 115 is diverted toward the surface of the specimen 114 via the first beam splitter 502 along the direct channel 507. Upon leaving the first beam splitter 502, the light from the illumination source 102 is then transmitted through the second beam splitter 508 and the main objective 109 toward the surface of the specimen 114 along the object path 112 which is collinear with the direction channel 507. Then, the impinging light is reflected from the surface of the specimen 114 and directed toward the imaging plane of the detector 110.

In a second configuration, when shutter 505 is closed (i.e., the direct channel 507 is blocked) and shutter 504 is open (i.e., the rotational channel 506 is open), the system 500 operates as an imaging microscope which rotates both the illumination pupil and the image of the wafer by 180°. In this manner, light from the illumination source 102 may travel through the rotational channel 506 to the second beam splitter 508. The second beam splitter 508 may then direct light from the output of the rotational channel 506 toward the surface of the specimen 114 via the objective 109. Upon impinging on the surface of the specimen 114, the rotationally transformed light may then be reflected toward the imaging plane of the detector 110. It is further recognized that a variety of additional optical elements commonly known in the may exist within the system 500, such as, but not limited to, intermediate lenses and imaging lenses.

In a third configuration, both shutter 505 and shutter 504 may be opened, allowing light from the illumination path 115 to be transmitted along both the rotational channel 506 and the direct channel 507. This configuration allows for a two beam interference-based focusing process to be carried out as light from the reference path 113 is allowed to interfere with light from the object path 112, creating interference fringes at the image plane of a focusing system (not shown). Details of two beam interference autofocusing systems are described in U.S. Pat. No. 4,818,110, issued on Apr. 4, 1989, and U.S. Pat. No. 6,172,349, issued on Jan. 9, 2001, which are incorporated herein by reference.

The system 500 described above may be utilized to carry out fast TSI measurements. In this manner, system 500 may perform two sequential measurements. The first measurement may be carried out with the direct channel 507, while the second measurement may be carried out via the rotational channel 506. First, the system 500 measures the contribution to TIS of the illumination source 102 and any optical elements positioned between the first beam splitter 502 and the detector 110, allowing a user to calibrate the TIS measurements by correcting for residual TIS. Applicant notes that the system 500 does not measure the TSI contribution due to the objective lens 109 or the TSI contributions from the abberative effects of the optical elements of the rotational channel. Consequently, the present fast TSI measurement system is most advantageous when the objective lens 109 and the optical elements of the rotational channel 506 are of high quality.

The system 500 may measure the TIS by measuring overlay sequentially at 0° and 180°. In this manner, the system may measure overlay at 0° (i.e., OVL(0) of equation 1) utilizing light from the direct channel 507 and then measuring overlay at 180° (i.e., OVL(180) of equation 1) rotation utilizing illumination from the rotational channel 506. In so doing, the measured TIS may be calculated utilizing equation 1 provided above.

It is further contemplated, however, that the TSI contribution of part of the objective lens 109 may be measured if the part of the objective closest to the specimen 114 includes a module capable of flipping in and out of the optical pathway in a short time and can act to rotate the image by 180 degrees. In this manner, the modified portion of the objective lens acts to replace the rotating module 210 located along the rotational channel 506. TIS measurement is carried out using two sequential measurements with and without the rotating module. Such an optical design would relax the optical requirements on the objective lens, leaving heightened optical requirements only for the rotating module of the objective.

It is further contemplated herein that the optical elements of the rotational channel 506 may be replaced by optical elements which perform transformations other than 180° degree rotation. For example, optical elements suitable for performing an x-y inversion on the illumination may be used to replace the optics depicted in the rotational channel 506 of FIG. 5A. The ability to apply different types of transformation operations on the light from the illumination source 102 is advantageous when the measurement of TIS is related to symmetry operations.

Referring now to FIG. 5B, an alternative embodiment of a system for tool induced shift measurement is illustrated. As in FIG. 5A, the system 501 of FIG. 5B may include, but is not limited to, an illumination source 102, a detector 110, a rotational channel 506, a direct channel 507, a first shutter 517, and a second shutter 518.

In one aspect, the direct channel 507 of the system 501 is formed by the pathway defined by the first beam splitter 513, the first mirror 514, and the second beam splitter 517. In another aspect, the rotational channel 506 of the system 501 is formed by the pathway defined by the first beam splitter 513, the rotational module 210, the second mirror 516, and the second beam splitter 517. As in system 500 described above, it should be recognized that illumination emanating from an illumination source 102 may pass between a first beam splitter 513 and a second beam splitter 517 via either the rotational channel 506 or the direct channel 507. The manner in which light passes along the direct channel 507 and/or the rotational channel may be controlled by controlling the shutters 517 and 518 respectively. The description above related to the operation of the TIS measurement system 500 should be interpreted to apply to system 501.

Figure 6:
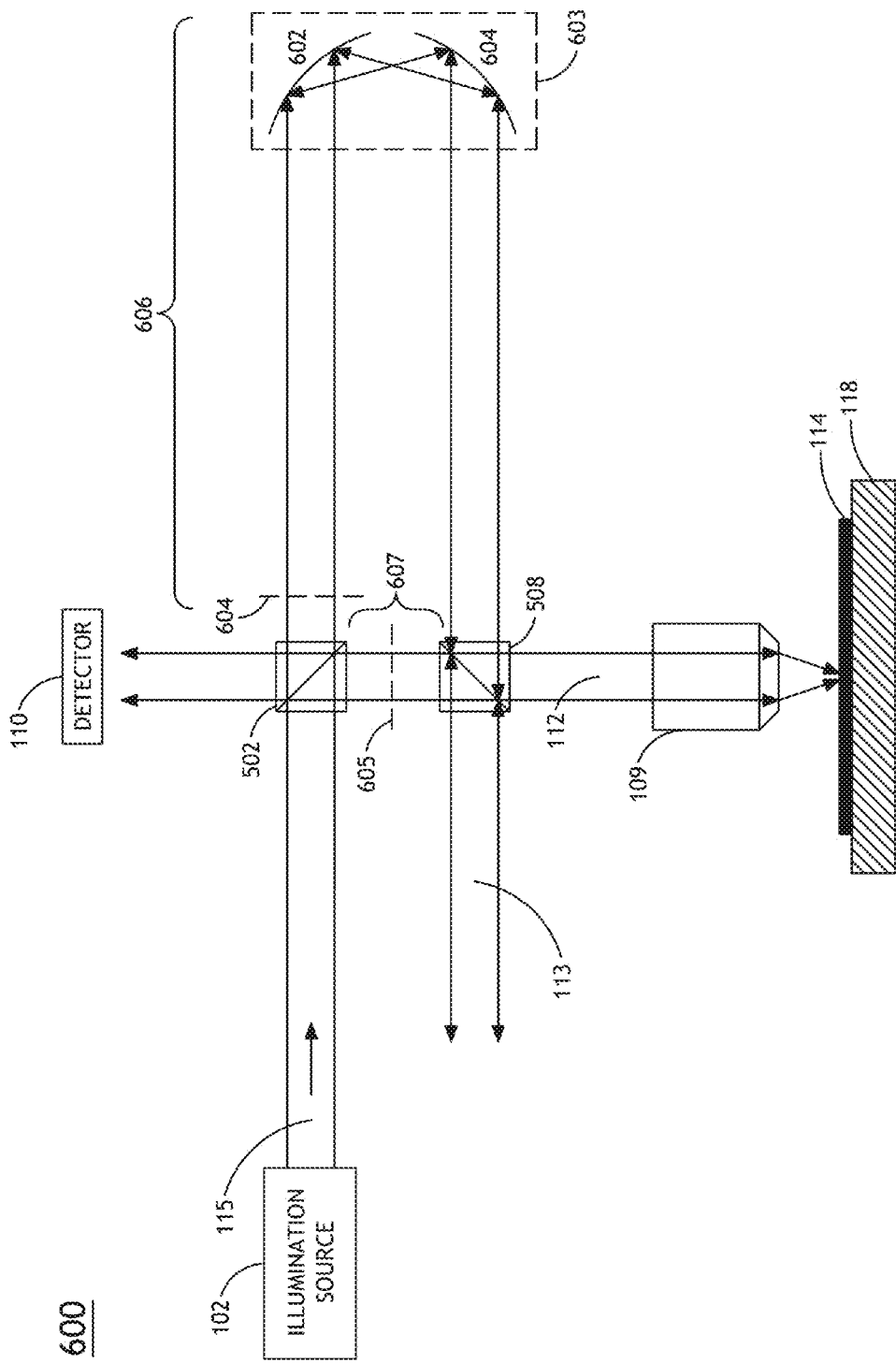
FIG. 6 illustrates a block diagram of an apparatus suitable for tool induced shift measurement in accordance with the present invention.

Referring now to FIG. 6, an alternative embodiment of a system for tool induced shift measurement is illustrated. The system 600 may include, but is not limited to, an illumination source 102, a detector 110, a rotational channel 606, a direct channel 607, a first shutter 604, and a second shutter 605. In contrast to the system 500 of the present invention, the rotational channel 606 of system 600 lacks a rotational module 506. Rather, the system 600 includes a reflection module 603 configured to perform a 180° rotation of an incident image. In one embodiment, the reflection module 603 may include a pair of concave mirrors, mirror 602 and mirror 601. The concave mirrors 602 and 601 may be arranged such that illumination incident on mirror 602 is reflected across both the X-axis and Y-axis of the image upon emerging from mirror 601, resulting in an image having a 180° rotated character. This 180° rotated illumination may then be utilized in fast TIS measurements as described above with respect to system 500. Therefore, the description above related to the operation of the TIS measurement system 500 should be interpreted to apply to system 600.

Figure 7A:
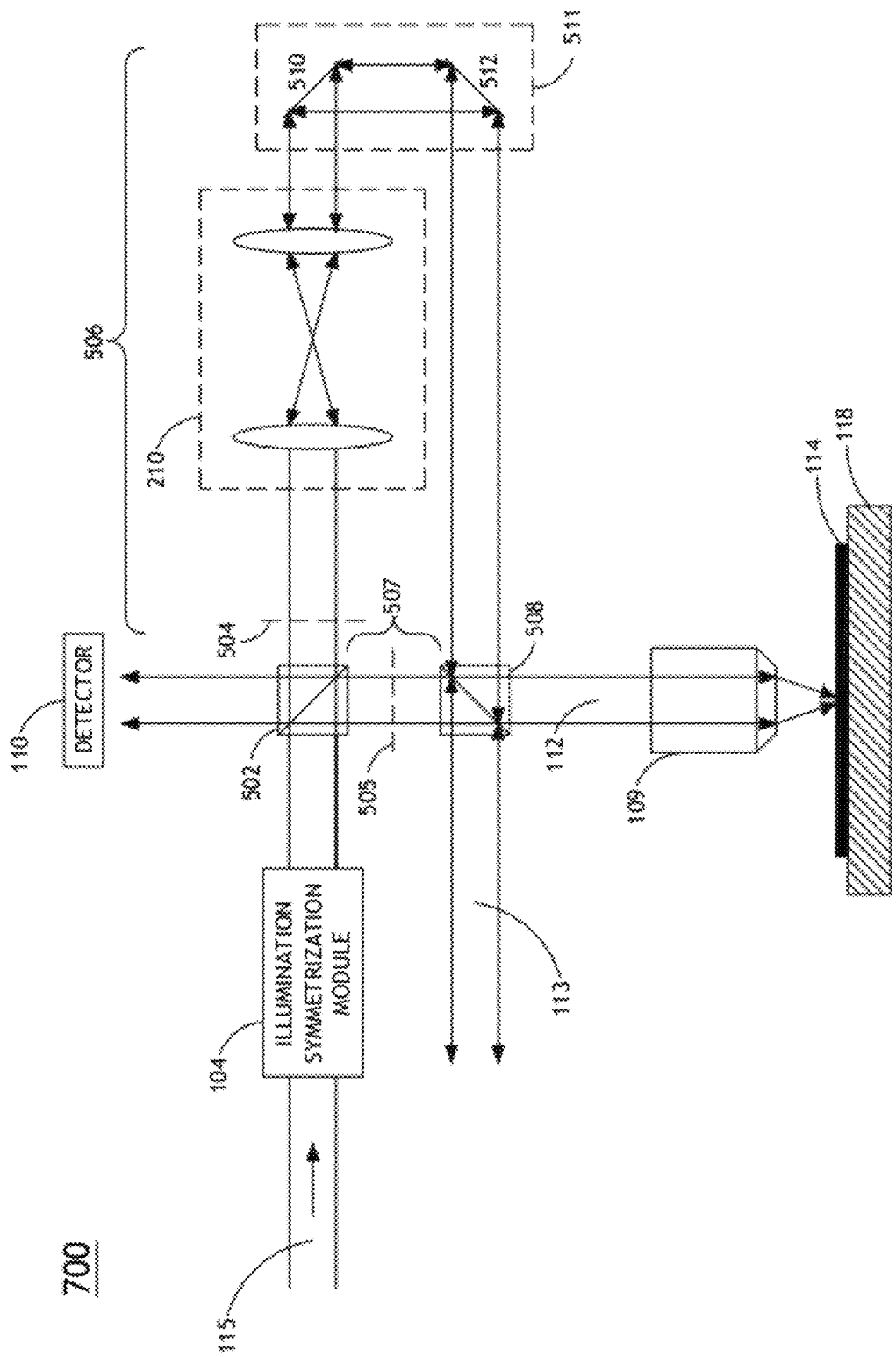
FIG. 7A illustrates a block diagram of an apparatus suitable for tool induced shift measurement implemented in concert with an illumination symmetrization module in accordance with the present invention.
Figure 7B:
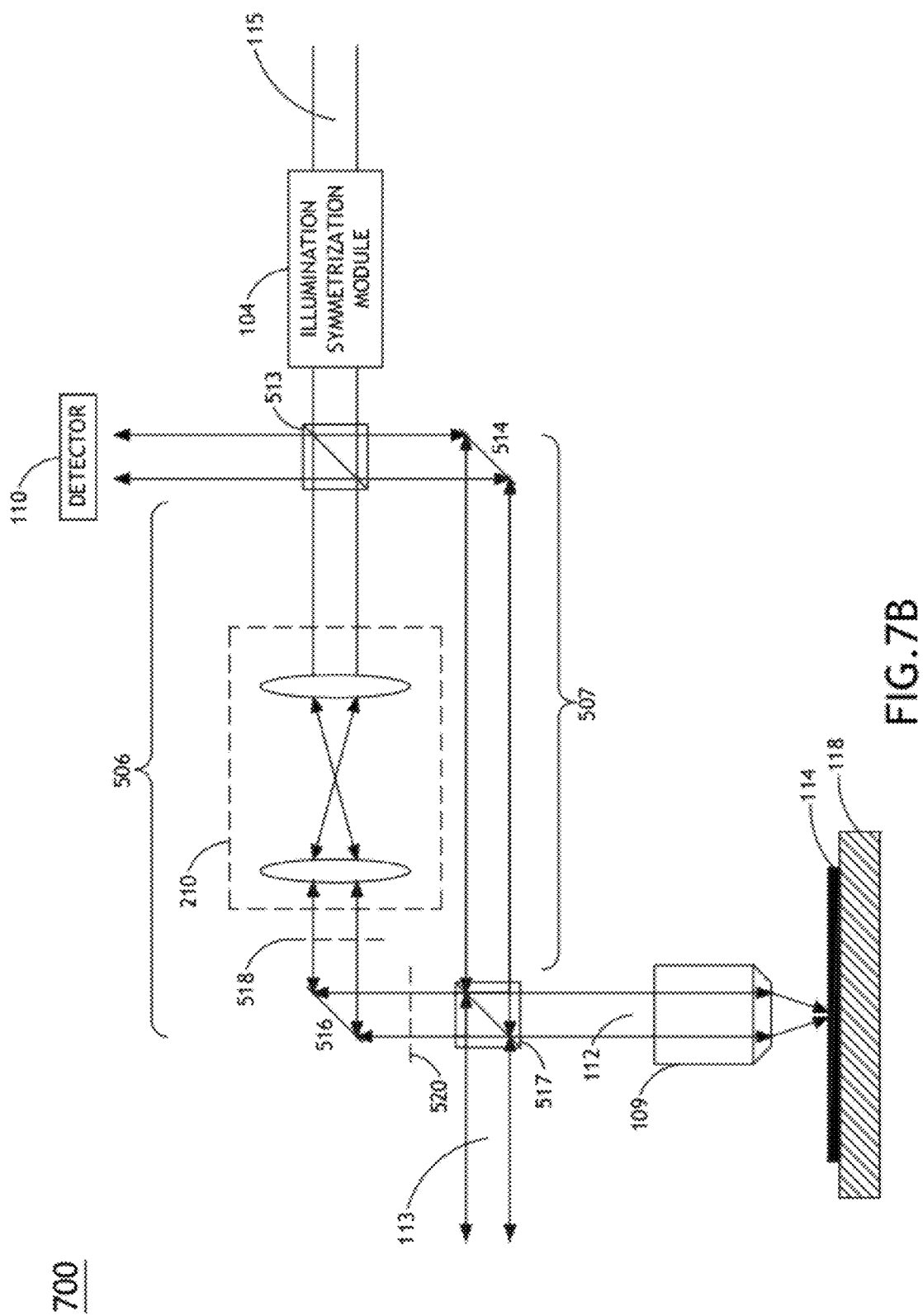
FIG. 7B illustrates a block diagram of an apparatus suitable for tool induced shift measurement implemented in concert with an illumination symmetrization module in accordance with the present invention.

Referring now to FIGS. 7A and 7B, it is further contemplated herein that the illumination symmetrization module 104 as described above may be implemented in context with a TIS measurement system 500, 501, or 600.

All of the system and methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

Furthermore, it is to be understood that the invention is defined by the appended claims.

What is claimed:

1. An apparatus, comprising:
an overlay metrology tool, the overlay metrology tool comprising:

an illumination source configured to generate continuous illumination;

a first beam splitter configured to direct a first portion of continuous illumination from the illumination source along a first optical arm and a second portion of continuous illumination along a second optical arm;

at least one illumination symmetrization module (ISM) positioned in the first optical arm, the ISM including one or more optical elements configured to apply a symmetrization process on the first portion of continuous illumination from the illumination source;

a second beam splitter configured to combine the first portion of continuous illumination from the first optical arm, following processing of the first portion of continuous illumination by the ISM, and the second portion of continuous illumination from the second optical arm to form a symmetrized continuous output beam such that tool induced shift of the optical metrology tool is at or below a selected level, wherein the second beam splitter is further configured to direct the symmetrized continuous output beam to a surface of one or more specimens; and a detector disposed along a primary optical axis of the overlay metrology tool, wherein the detector is configured to collect a portion of illumination reflected from the surface of the one or more specimens wherein the at least one ISM comprises:

a 180 degree symmetrization module configured to perform a 180 degree rotational symmetrization transformation on the first portion of continuous illumination form the illumination source.

2. The apparatus of claim 1, wherein the at least one ISM comprises:

a Y-reflection symmetrization module configured to perform a Y-reflection symmetrization transformation on illumination emanating from the illumination source.

3. The apparatus of claim 1, wherein the at least one ISM comprises:

a first ISM and at least a second ISM, wherein the first ISM and the at least a second ISM are combined in series such that an output of the first ISM is optically coupled to an input of the at least a second ISM.

4. The apparatus of claim 1, wherein the at least one ISM comprises:

a first ISM and at least a second ISM, wherein the first ISM and the at least a second ISM are combined in series such that an output of the first ISM is optically coupled to an input of the at least a second ISM, wherein the first ISM is substantially the same as the second ISM.

5. The apparatus of claim 1, wherein the at least one ISM comprises:

a first ISM and at least a second ISM, wherein the first ISM and the at least a second ISM are combined in series such that an output of the first ISM is optically coupled to an input of the at least a second ISM, wherein the first ISM is different than the second ISM.

6. The apparatus of claim 1, wherein the object path and the reference path form a portion of a two-beam interferometric focusing system.

7. The apparatus of claim 1, wherein the object path and the reference path form a portion of a two-beam interferometric focusing system a Linnik interferometer.

8. An apparatus for measuring tool induced shift, comprising:

an overlay metrology tool, the overlay metrology tool comprising:

an illumination source;

a direct channel configured to transmit a first portion of light emanating from the illumination source to a surface of one or more specimens;

a rotational channel configured to transmit a second portion of light emanating from the illumination source to a the surface of one or more specimens, wherein the rotational channel includes an optical rotation module configured to rotate the second portion of light by 180 degrees;

a first shutter configured to selectively block an optical pathway of the rotational channel;

a second shutter configured to selectively block an optical pathway of the direct channel;

a detector, wherein the detector is configured to selectively collect light from the direct channel reflected from the surface of the one or more specimens and light from the rotational channel reflected from the surface of the one or more specimens based on the selective control of the first shutter and second shutter; and a computing system configured to determine tool induced shift within the overlay metrology tool by comparing light collected from the direct channel and light collected from the rotational channel.

9. The apparatus of claim 8, wherein the optical rotation module of the rotational channel includes a one-to-one rotational imaging module.

10. The apparatus of claim 8, wherein the rotational channel includes an optics return module.

11. The apparatus of claim 9, wherein the optics return module includes a set of planar mirrors configured to direct light of the rotational channel toward an objective lens.

12. The apparatus of claim 8, further comprising:

a first beam splitter configured to perform at least one of direct light emanating from the illumination source along the direct channel or transmit light emanating from the illumination source toward the surface of the specimen.

13. The apparatus of claim 8, further comprising:

a second beam splitter configured to perform at least one of direct light emerging from the rotational channel toward the surface of the specimen or transmit light along a reference path.

14. The apparatus of claim 8, further comprising:

at least one illumination symmetrization module.

15. The apparatus of claim 14, wherein the at least one illumination symmetrization module comprises:

at least one illumination symmetrization module configured to process light emanating from the illumination source prior to entering the rotational channel.

* * * * *